United States Patent [19]

Iizuka et al.

[11] Patent Number: 4,486,597
[45] Date of Patent: Dec. 4, 1984

[54] METHOD FOR THE PRODUCTION OF NUCLEAR SUBSTITUTED CINNAMOYLANTHRANILIC ACID DERIVATIVES

[75] Inventors: Kinji Iizuka, Matsumoto; Tetsuhide Kamino, Shiojiri; Ryoji Yamamoto; Hiromu Harada, both of Matsumoto, all of Japan

[73] Assignee: Kissei Pharmaceutical Co., Ltd., Japan

[21] Appl. No.: 577,758

[22] Filed: Feb. 7, 1984

Related U.S. Application Data

[63] Continuation of Ser. No. 405,159, Aug. 4, 1982.

[30] Foreign Application Priority Data

Sep. 1, 1981 [JP] Japan ............................... 56-137344

[51] Int. Cl.$^3$ ............................................. C07C 99/00
[52] U.S. Cl. .................................................. 562/455
[58] Field of Search ....................... 562/455, 453, 457

[56] References Cited

U.S. PATENT DOCUMENTS 3,755,603 8/1973 Harrison et al. .................... 424/317
4,337,270 6/1982 Noda et al. ......................... 562/453

FOREIGN PATENT DOCUMENTS 818858 1/1981 Japan ................................. 562/455

Primary Examiner—James H. Reamer
Attorney, Agent, or Firm—Depaoli & O'Brien

[57] ABSTRACT

The present invention provides an improved method for producing a nuclear substituted cinnamoylanthranilic acid compound.

Illustrative of the process is the reaction of 3,4-dimethoxybenzaldehyde with 2-carboxymalonanilic acid in an inert solvent medium in the presence of piperidine to provide an intermediate salt precipitate, and the salt is treated with an acidic reagent to yield N-(3,4-dimethoxycinnamoyl)anthranilic acid product.

9 Claims, No Drawings

METHOD FOR THE PRODUCTION OF NUCLEAR SUBSTITUTED CINNAMOYLANTHRANILIC ACID DERIVATIVES

This is a continuation, of application Ser. No. 405,159, filed Aug. 4, 1982.

BACKGROUND OF THE INVENTION

1. Field of the Invention

This invention relates to a novel method for the production of nuclear substituted cinnamoylanthranilic acid derivatives. More particularly, this invention relates to an improved method for the production of nuclear di-substituted cinnamoylanthranilic acid derivatives which possess strong antiallergic properties and thus are useful for treatment of diseases such as asthma, hay fever, atopic dermatitis and urticaria.

2. Description of the Prior Art

Nuclear substituted cinnamoylanthranilic acid derivatives, especially N-(3,4-dimethoxycinnamoyl)anthranilic acid, are known to exhibit strong antiallergic properties and to be useful for treatment of asthma, hay fever, atopic dermatitis and urticaria, as reported in U.S. Pat. No. 4,070,484; Allergy, 34, 213–219, (1979); and Igaku no Ayumi, 106, No. 8, 576–585 (1978).

Several methods for producing said derivatives have been also disclosed in Japanese patent application Nos. 7359/73, 42273/74, 42465/74, 43673/74, 43678/74, 158554/75, 158555/75, 158556/75, 139368/76, 38555/80, 38556/80 and 8858/81, and in U.S. Pat. No. 3,940,422. Of the methods disclosed in the above patent references, the process described in Japanese patent application No. 8858/81 can be operated with ease and efficiency, and thus this process has advantage for production on an industrial scale. The Japanese patent application No. 8858/81 invention is illustrated by the following preferred process embodiment.

A nuclear unsubstituted or substituted benzaldehyde derivative is heated with a 2-carboxymalonanilic acid derivative at 80°–100° C. for several hours in a solvent medium such as pyridine; or benzene, toluene or xylene (10–20 times by weight the amount of the benzaldehyde derivative or the 2-carboxymalonanilic acid derivative) in the presence of a catalytic amount of a basic compound such as piperidine. The resultant reaction mixture is evaporated and the residue is dissolved in a small amount of an alcohol. The alcoholic solution is poured into ice-water, then hydrochloric acid is added to make the aqueous medium acidic, and the crystalline precipitate which forms is collected by filtration and recrystallized from a suitable organic solvent to yield the desired product.

As apparent from the above described procedure, the process embodiment requires the use of a large volume of pyridine solvent as a reaction medium. This is undesirable because in addition to the cost involved pyridine solvent has the disadvantages of toxicity and odor. Furthermore, since the desired product is obtained as a precipitate from an aqueous acidic solution of the evaporated reaction mixture by acidification with a mineral acid, unreacted materials and byproducts which are insoluble in an aqueous acidic solution are also precipitated, and these components are difficult to remove by recrystallization and thus are contained in the desired product. Hence, the desired product purified by recrystallization always contains such impurities and is not applicable for medicinal purposes without an extensive recrystallization procedure, with a concomitant decrease in product yield.

Accordingly, it is an object of this invention to provide a process for producing anthranilic acid derivatives which is superior to prior art methods such as that described in Japanese patent application No. 8858/81.

It is another object of this invention to provide an improved method for producing nuclear di-substituted cinnamoylanthranilic acid derivatives with a high purity and yield, which derivatives possess strong antiallergic properties and thus are useful for treatment of asthma, hay fever, atopic dermatitis and urticaria.

Other objects and advantages of this invention will become apparent from the accompanying description and examples.

DESCRIPTION OF THE INVENTION

This invention provides an improved method for the production of nuclear substituted cinnamoylanthranilic acid derivatives corresponding to the formula:

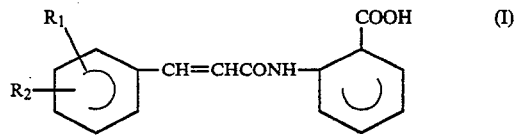

where $R_1$ and $R_2$ may be the same or different, and each represents a hydroxy or an alkoxy substituent having about 1–3 carbon atoms. The said derivatives possess strong antiallergic properties, and are useful for treatment of diseases caused by allergies, such as asthma, hay fever, atopic dermatitis and urticaria.

Thus, one or more objects of the present invention are accomplished by the provision of a process which comprises reacting a nuclear di-substituted benzaldehyde corresponding to the formula:

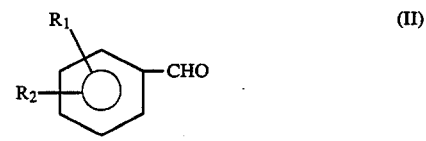

where $R_1$ and $R_2$ are substituents as previously defined, in an inert organic solvent with 2-carboxymalonanilic acid corresponding to the formula:

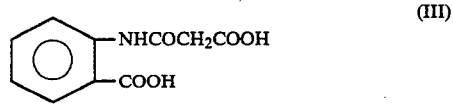

and a cyclic amine corresponding to the formula:

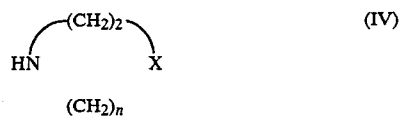

where X is a methylene group or an oxygen atom, n is 1 or 2 with the proviso that n is 2 when X is an oxygen atom, said cyclic amine being employed in an equimolar amount to the nuclear substituted benzaldehyde derivative of formula(II) or the 2-carboxymalonanilic acid of Formula(III) above, to produce a compound corresponding to the formula:

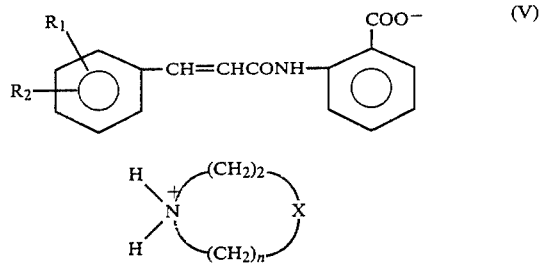

where $R_1$, $R_2$, X and n are as previously defined; and treating the said compound (V) under acidic conditions to yield a product corresponding to formula(I) above.

In general, as disclosed in the Japanese patent application No. 8858/81, this type of reaction is conducted in the presence of a catalytic amount of an amine such as piperidine, morpholine, methylamine, ethylamine, pyridine and the like. However, as described above, in the present invention process a specific type of cyclic amine compound is utilized in an equimolar amount as to the starting material of formula(II) or (III) above. By employing equimolar amounts of the cyclic amine and benzaldehyde(II) or 2-carboxymalonanilic acid(III) compounds in an inert organic solvent as a reaction medium, the intermediate of formula(V), i.e., the salt of nuclear substituted cinnamoylanthranilic acid derivative and cyclic amine, precipitates as crystals from the reaction mixture as the reaction proceeds, and thereafter is readily recovered in high yield from the reaction mixture. As a further advantage, the crystalline compound(V) is relatively free of unreacted materials and byproducts and can be converted easily into the desired free acid product in a high purity form by treatment with an acidic reagent such as a mineral acid.

Thus, in accordance with the present invention, the problems associated with the procedure disclosed in Japanese patent application No. 8858/81 are eliminated, and nuclear substituted cinnamoylanthranilic acid derivatives are prepared efficiently in high yield and purity.

Illustrative of inert organic solvents suitable in the invention process (i.e., solvents which crystallize the intermediate(V) as the reaction proceeds) are benzene, toluene, xylene, ethyl acetate and chloroform. Preferred inert organic solvents are aromatic hydrocarbons such as benzene and toluene.

The cyclic amine component employed in the invention process has to possess a catalytic property for condensing a nuclear di-substituted benzaldehyde derivative and 2-carboxymalonanilic acid, and has to possess properties for the formation of insoluble salt of cinnamoylanthranilic acid derivative in an inert solvent medium. Suitable cyclic amines include pyrrolidine, piperidine and morpholine, and the most preferred cyclic amine is piperidine.

Acid reagents suitable for the conversion of the intermediate(V) compound above into the desired compound(I) include inorganic acids such as hydrochloric acid, sulfuric acid, and the like, and organic acids such as acetic acid or p-toluenesulfonic acid. The use of a mineral acid such as hydrochloric acid is preferred.

The nuclear di-substituted benzaldehyde derivatives corresponding to formula(II) which are employed as a starting material are known compounds, and methods of synthesis are described in the chemical literature. Examples of said aldehydes include 2,3-, 2,4-, 2,5-, 2,6-, 3,4- and 3,5-dihydroxybenzaldehyde; 2,3-, 2,4-, 2,5-, 2,6-, 3,4- and 3,5-dimethoxybenzaldehyde; 2,3-, 2,4-, 2,5, 3,4- and 3,5-diethoxybenzaldehyde; 2,3-, 2,4-, 2,5-, 3,4- and 3,5-dipropoxybenzaldehyde; 2-hydroxy-3-methoxybenzaldehyde; 3-hydroxy-4-methoxybenzaldehyde; 3-ethoxy-4-methoxybenzaldehyde; 3-methoxy-4-propoxybenzaldehyde; 3-propoxy-4-methoxybenzaldehyde; and the like.

2-Carboxymalonanilic acid used as a starting material is also a known compound, and can be prepared according to the method described in Japanese application No. 43678/74.

In the method of this invention, since dehydration and decarboxylation reactions occur simultaneously with the formation of the intermediate compound corresponding to formula(V) above, the reaction preferably is conducted with continuous removal of water formed during the reaction course.

As a general procedure, a mixture of a benzaldehyde derivative corresponding to formula(II), 2-carboxymalonanilic acid, and a cyclic amine corresponding to formula(IV) (e.g., piperidine) in an equimolar amount to the benzaldehyde derivative(II) or 2-carboxymalonanilic acid(III) is dissolved in an inert organic solvent (e.g., benzene or toluene) in a proportion of about 1–3 liters of solvent per mole of benzaldehyde derivative, and then the resultant reaction solution is heated under reflux for a period of about 3–5 hours with continuous removal of water as it is formed during the reaction.

After cooling, the precipitated intermediate product is recovered by filtration and dissolved with heating in water. The resultant aqueous solution is added dropwise to a dilute hydrochloric acid solution. The crystalline product which precipitates is collected by filtration, and optionally, recrystallized from an organic solvent to provide the desired product corresponding to formula(I).

It is an advantage of the invention process that the cyclic amine that is utilized can be recovered from the filtrate and recycled in the process.

The present invention process is an improved method adapted for producing nuclear di-substituted cinnamoylanthranilic acid derivatives which possess strong antiallergic properties and which are useful for treatment of asthma, hay fever, atopic dermatitis and urticaria.

The following Examples are further illustrative of the present invention. The catalysts and other specific ingredients and processing parameters are presented as being typical, and various modifications can be derived in view of the foregoing disclosure within the scope of the invention.

EXAMPLE I

A.

A solution of 8.4 g of 3,4-dimethoxybenzaldehyde, 11.4 g of 2-carboxymalonanilic acid, and 4.3 g of piperidine in 50 ml of benzene is heated under reflux for 3 hours with the removal of water as formed during the reaction period. After the completion of the reaction, the reaction mixture is cooled and the precipitated crystals are collected by filtration and dried to obtain 19.7 g of piperidinium N-(3,4-dimethoxycinnamoyl)anthranilate (95.8% yield), m.p. 154°–156° C. The compound structure is confirmed by elemental analysis, and by IR and NMR spectroscopy.

B.

A solution of 8.4 g of 3,4-dimethoxybenzaldehyde, 11.4 g of 2-carboxymalonanilic acid, and 4.3 g of piperidine in 50 ml of toluene is heated for 3 hours under reflux with continuous removal of water during the reaction period. After the completion of the reaction, the reaction mixture is cooled and the precipitated crystals are collected by filtration and dried to obtain 19.5 g of piperidinium N-(3,4-dimethoxycinnamoyl)anthranilate (94.8% yield), as confirmed by elemental analysis and spectroscopy.

EXAMPLE II

A solution of 8.4 g of 3,4-dimethoxybenzaldehyde, 11.4 g of 2-carboxymalonanilic acid, and 4.4 g of morpholine in 50 ml of benzene is heated for 3 hours under reflux with removal of water as it is formed during the reaction.

After the completion of the reaction, the reaction mixture is cooled and the precipitated crystals are collected by filtration to obtain 19.5 g of morpholinium N-(3,4-dimethoxycinnamoyl)anthranilate (94.2% yield), m.p. 132°–136° C. The compound structure is confirmed by elemental analysis, and by IR and NMR spectroscopy.

EXAMPLE III

A solution of 8.4 g of 3,4-dimethoxybenzaldehyde, 11.4 g of 2-carboxymalonanilic acid, and 3.56 g of pyrrolidine in 50 ml of benzene is heated for 3 hours under reflux with removal of water of reaction.

After completion of the reaction, the mixture is cooled and the precipitated crystals are collected by filtration and dried to obtain 18.6 g of pyrrolidinium N-(3,4-dimethoxycinnamoyl)anthranilate (93.4% yield), m.p. 141°–142° C. The compound structure is confirmed by IR and NMR spectroscopy, and by elemental analysis.

EXAMPLE IV

A solution of 2.54 g of vanillin, 3.8 g of 2-carboxymalonanilic acid, and 1.43 g of piperidine in 20 ml of benzene is heated for 3 hours under reflux with removal of water of reaction. After completion of the reaction, the reaction mixture is cooled and the precipitated crystals are collected by filtration and dried to obtain 6.3 g of piperidinium N-(4-hydroxy-3-methoxycinnamoyl)anthranilate (94.7% yield), m.p. 188°–189° C. The compound structure is confirmed by elemental analysis, and by IR and NMR spectroscopy.

EXAMPLE V

A solution of 2.3 g of 3,4-dihydroxybenzaldehyde, 3.8 g of 2-carboxymalonanilic acid, and 1.43 g of piperidine in 50 ml of benzene is heated for 3 hours under reflux with removal of water of reaction.

After the completion of the reaction, the reaction mixture is cooled and the precipitated crystals are collected by filtration and recrystallized from ethanol to obtain 3.8 g of piperidinium N-(3,4-dihydroxycinnamoyl)anthranilate as pale yellow crystals (59.2% yield), m.p. 206°–208° C. The compound structure is confirmed by elemental analysis, and IR and NMR spectroscopy.

EXAMPLE VI

A 20 g quantity of piperidinium N-(3,4-dimethoxycinnamoyl)anthranilate is dissolved in 60 ml of water with heating, and the resultant aqueous solution is added dropwise to 45 ml of diluted hydrochloric acid (5 ml of conc. hydrochloric acid and 40 ml of water) with stirring. The precipitated crystals which form are collected by filtration, washed with water and then dried at 90°–100° C. under reduced pressure for 3 hours to yield 15.5 g of N-(3,4-dimethoxycinnamoyl)anthranilic acid (98.0% yield), m.p. 208°–208.5° C. The compound structure is confirmed by elemental analysis, and by IR and NMR spectroscopy.

EXAMPLE VII

A 20 g quantity of morpholinium N-(3,4-dimethoxycinnamoyl)anthranilate is dissolved in 40 ml of water and the resultant solution is added dropwise to 45 ml of diluted hydrochloric acid (5 ml of conc. hydrochloric acid and 40 ml of water) with stirring. The precipitated crystals which form are collected by filtration, washed with water and then dried at 90°–100° C. under reduced pressure for 3 hours to yield 15.5 g of N-(3,4-dimethoxycinnamoyl)anthranilic acid (98% yield). The compound is confirmed as identical to that obtained in EXAMPLE VI.

What is claimed is:

1. A process for the production of a nuclear substituted cinnamoylanthranilic acid derivative corresponding to the formula:

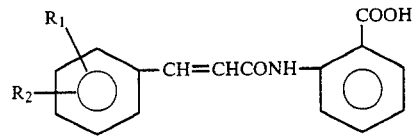

where each of $R_1$ and $R_2$ is an alkoxy group having about 1-3 carbon atoms, which process comprises (1) reacting in an inert organic solvent medium a nuclear substituted benzaldehyde derivative corresponding to the formula:

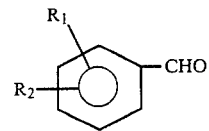

where $R_1$ and $R_2$ are as previously defined, with 2-carboxymalonanilic acid and a cyclic amine corresponding to the formula:

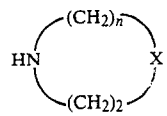

where X is a methylene group or an oxygen atom, n is 1 or 2 with the proviso that n is 2 when X is an oxygen atom, and said cyclic amine is employed in about an equimolar amount with respect to the substituted benzaldehyde derivative reactant or 2-carboxymalonanilic acid reactant, to produce an intermediate crystalline precipitate of a compound corresponding to the formula:

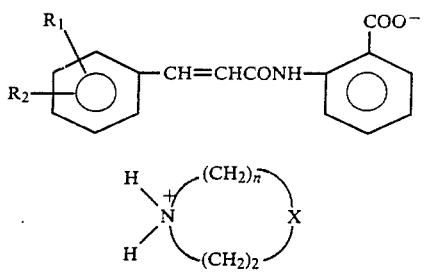

where $R_1$, $R_2$, n and X are as previously defined; and (2) treating the intermediate compound with an acidic reagent to yield a nuclear substituted cinnamoylanthranilic acid product corresponding to the formula above.

2. A process in accordance with claim 1 wherein water of reaction is removed from the reaction zone during the heating period.

3. A process in accordance with claim 1 wherein the inert organic solvent is an aromatic hydrocarbon.

4. A process in accordance with claim 1 wherein the inert organic solvent is benzene or toluene.

5. A process in accordance with claim 1 wherein the benzaldehyde reactant is 3,4-dimethoxybenzaldehyde.

6. A process in accordance with claim 1 wherein the cyclic amine is piperidine.

7. A process in accordance with claim 1 wherein the cyclic amine is morpholine.

8. A process in accordance with claim 1 wherein the cyclic amine is pyrrolidine.

9. A process in accordance with claim 1 wherein the nuclear substituted cinnamoylanthranilic acid product is N-(3,4-dimethoxycinnamoyl)anthranilic acid.

* * * * *

UNITED STATES PATENT OFFICE
CERTIFICATE OF CORRECTION

Patent No. 4,486,597                Dated December 4, 1984

Inventor(s) Iizuka et al

It is certified that error appears in the above-identified patent and that said Letters Patent are hereby corrected as shown below:

Column 2, line 25, the formula should be completed by closing the inner circles within the benzene structures.

Signed and Sealed this

Twenty-ninth Day of October 1985

[SEAL]

Attest:

Attesting Officer

DONALD J. QUIGG

Commissioner of Patents and
Trademarks—Designate